United States Patent [19]

Krasnow

[11] 4,126,418
[45] Nov. 21, 1978

[54] CUVETTE

[75] Inventor: Leonard L. Krasnow, Westboro, Mass.

[73] Assignee: Elkay Products, Inc., Shrewsbury, Mass.

[21] Appl. No.: 819,970

[22] Filed: Jul. 28, 1977

Related U.S. Application Data

[63] Continuation of Ser. No. 676,068, Apr. 12, 1976, abandoned.

[51] Int. Cl.² ................ B65B 43/42; B67C 3/00; G01N 1/00
[52] U.S. Cl. ................... 422/64; 141/130; 211/89
[58] Field of Search .............. 23/259, 253 R, 230 R; 211/78, 89; 141/130

[56] References Cited

U.S. PATENT DOCUMENTS

| | | | |
|---|---|---|---|
| 3,190,731 | 6/1965 | Weiskopf | 23/259 X |
| 3,192,968 | 7/1965 | Baruch et al. | 23/259 X |
| 3,549,330 | 12/1970 | Jungner et al. | 23/259 |
| 3,705,788 | 12/1972 | Kolko et al. | 23/259 |
| 3,832,135 | 8/1974 | Drozdowski et al. | 23/230 R |
| 3,897,216 | 7/1975 | Jones | 23/259 |
| 3,905,482 | 9/1975 | Knulst | 23/259 X |

Primary Examiner—Robert M. Reese
Attorney, Agent, or Firm—Norman S. Blodgett; Gerry A. Blodgett

[57] ABSTRACT

Curvette of generally circular form having apertures adjacent the outer periphery and having a plurality of compartment elements formed of an optically-clear plastic snugly locked in the apertures.

14 Claims, 6 Drawing Figures

CUVETTE

This is a continuation of application Ser. No. 676,068 filed Apr. 12, 1976, and now abandoned.

BACKGROUND OF THE INVENTION

In the operation of a medical laboratory, one of the routine operations is the performing of tests on samples of blood or urine. In order to facilitate such operations, it is common practice to use a carrousel or multi-station type machine that subjects a sample vial or curvette to a succession of tests as it is moved from station to station. The primative versions of such machines made use of individual sample vials dropped into sockets on a large horizontal rotatable disk, but the more modern versions of this type of chemical analysis machine have used a so-called "multi-cuvette" in which the sample vials are formed at an integral part of a larger rotatable body. Although in some respects such an integral apparatus is convenient, there are a number of drawbacks. Because some of the analytic tests involve optics, the sample vial must be made of an optically-clear plastic; this means that, in the multi-cuvette described above, the entire apparatus must be made of an optically-clear plastic. This means that the apparatus must necessarily be quite costly, because of the expensive nature of any plastic which is both strong and also optically clear. Also, the problem arises that, when the user has run samples through the machine on only a few of the vials, he may easily forget which is the next vial in line that has not been used (and, therefore, is still clean). Furthermore, since the samples cannot be allowed to stand in the vials for any great length of time, it may be necessary to remove the entire multi-cuvette in order to empty the old samples. This may take place at a time when only a few vials have been used, thus resulting in a waste of the unused portion of the multi-cuvette. These and other difficulties experienced with the prior art devices have been obviated in a novel manner by the present invention.

It is, therefore, an outstanding object of the invention to provide a cuvette which is relatively inexpensive to manufacture, because portions of the apparatus can be molded from inexpensive plastic.

Another object of this invention is the provision of a cuvette of the multi-cell type in which the main body is made of an opaque, strong plastic and the individual sample vials are made from an optically clear plastic.

A further object of the present invention is the provision of a multi-cuvette in which individual sample vials can be readily removed and replaced.

It is another object of the instant invention to provide a multi-cuvette in which individual sample vials can be emptied of specimen without disturbing the remainder of the vials.

A still further object of the invention is the provision of a cuvette of the multi-cell type in which each cell is positively identified.

It is a further object of the invention to provide a cuvette of the type having a plurality of sample vials accurately located in a main body and locked against accidental removal.

With these and other objects in view, as will be apparent to those skilled in the art, the invention resides in the combination of parts set forth in the specification and covered by the claims appended hereto.

SUMMARY OF THE INVENTION

In general, the present invention consists of a cuvette for use in chemical analysis, the cuvette having a main body with a central bore to permit mounting for rotation about the axis of the bore. A flange extends radially outwardly in a general plane perpendicular to the axis of the bore, the flange being formed with a plurality of apertures located at equal spacing about the axis. A plurality of compartment elements are formed of an optically-clear polymer, each element being in the form of an upwardly-opening container whose surface around the upper edge fits snugly in an aperture in the flange.

More specifically, the compartment element is provided with an outwardly-extending ridge that rests on the surface of the flange along the edge of the aperture. At least one abutment such as a pair of buttons are located on opposite portions of the aperture to lock the compartment element in an aperture and to resist dislodgement therefrom.

BRIEF DESCRIPTION OF THE DRAWINGS

The character of the invention, however, may be best understood by reference to one of its structural forms, as illustrated by the accompanying drawings, in which.

DESCRIPTION OF THE PREFERRED EMBODIMENT

Figure 1:
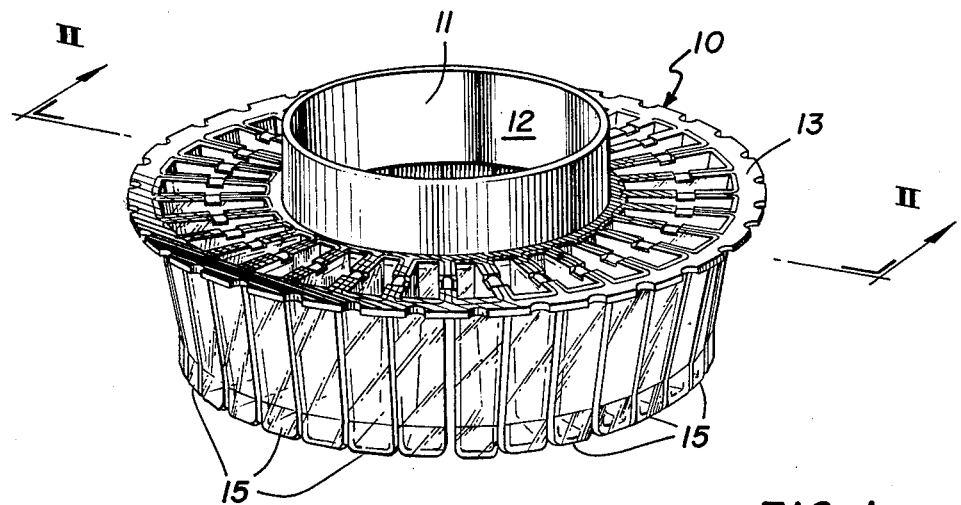
FIG. 1 is a perspective view of a cuvette constructed in accordance with the principles of the present invention.
Figure 2:
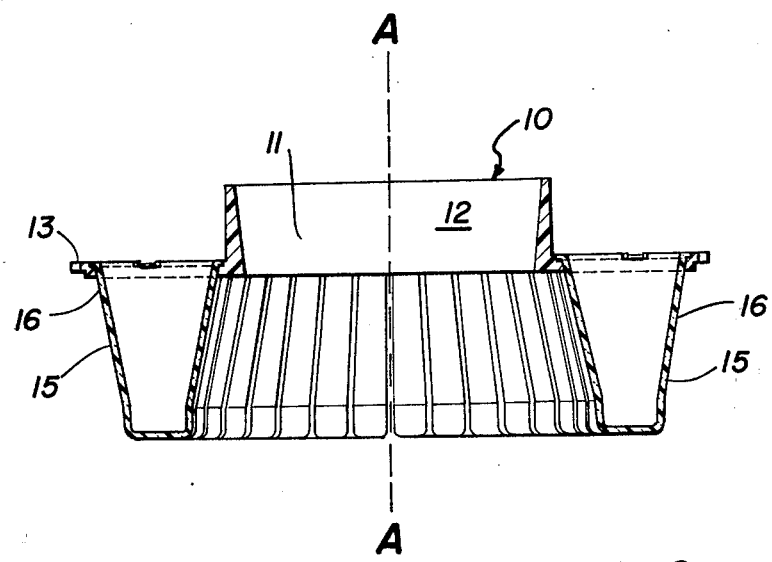
FIG. 2 is a vertical sectional view of the cuvette taken on the line II—II of FIG. 1.

Referring first to FIG. 1, wherein are best shown the general features of the invention, the cuvette, indicated generally by the reference numeral 10, is shown as having a main body 11 with a central bore 12 to permit mounting on an analysis machine for rotation about the axis A—A of the bore. The flange 13 extends radially outwardly in a horizontal plane generally perpendicular to the axis A—A and is formed with a plurality of apertures 14 located at equal spacing about the axis.

A plurality of compartment elements 15 are provided formed of an optically-clear polymer. Each element is in the form of an upwardly-opening container whose outer surface 16 around the upper edge fits snugly in an aperture 14. In the preferred embodiment, the main body 11 is formed of the tough and strong opaque plastic, such as ABS, while each compartment element 15 is formed of an optically-clear plastic, such as an acrylic plastic.

Figure 3:
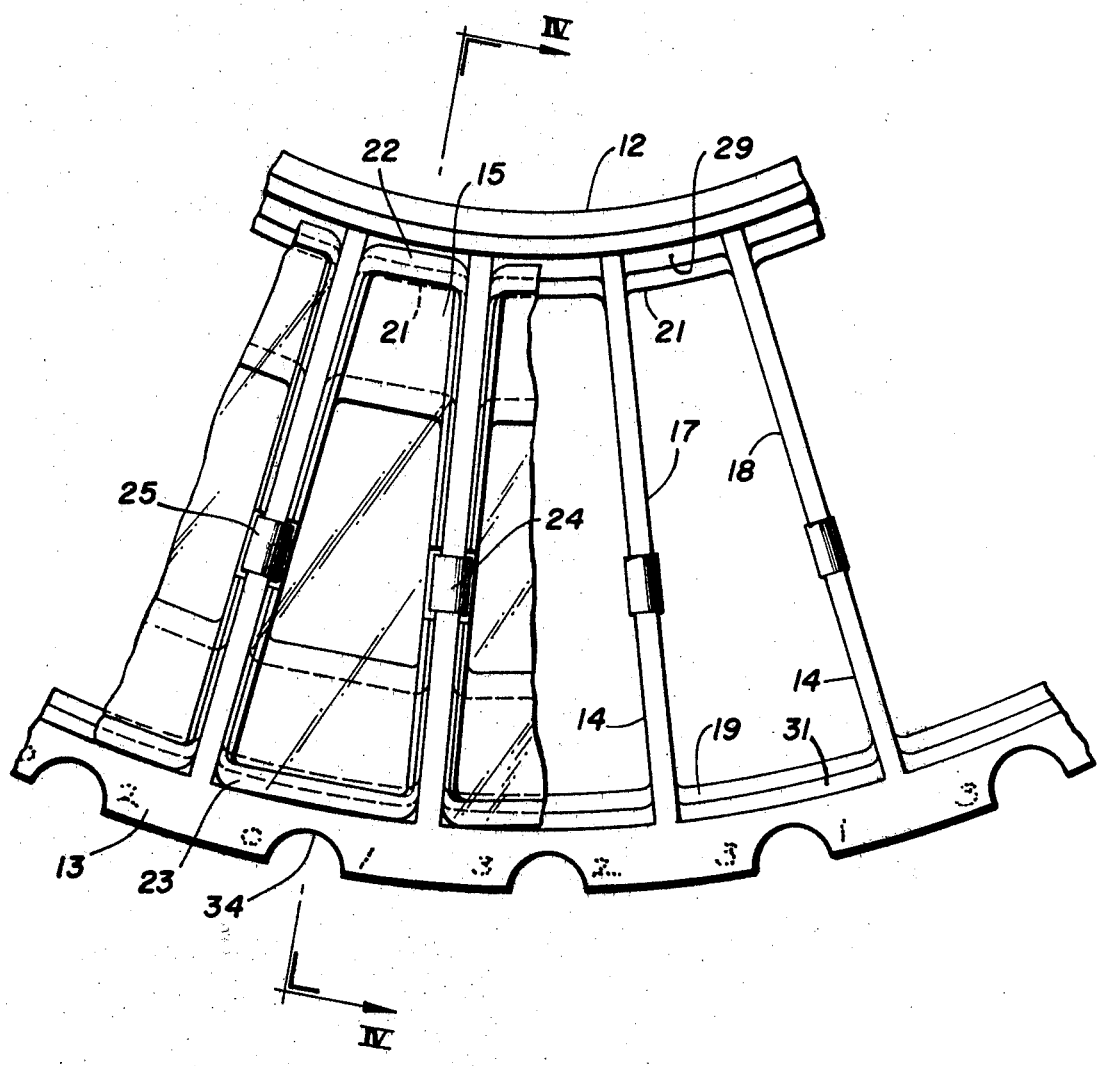
FIG. 3 is a plan view of the cuvette with portions broken away or removed.

Referring next to FIG. 3, it can be seen that each aperture 14 is in the general form of a trapezoid having elongated sides 17 and 18 extending generally radially of the axis A—A. A short base 19 is located along the outer periphery of the flange and an even shorter side 21 is located inwardly of the flange.

The compartment element 15 is provided with outwardly-extending ridges 22 and 23 that rest on the surface of the flange along the bases 22 and 23, respectively, of the edge of the aperture. Buttons 24 and 25 are provided to lock the compartment element 15 in an aperture 14 to resist dislodgement therefrom. These buttons 24 and 25 are located on the opposite sides 18 and 17, respectively, of the aperture.

Figure 5:
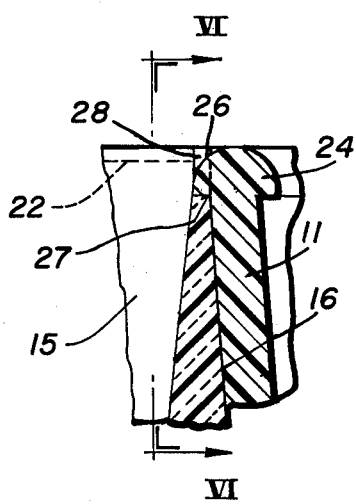
FIG. 5 is an enlarged vertical sectional view of a portion of the cuvette taken on the line V—V in FIG. 4.
Figure 6:
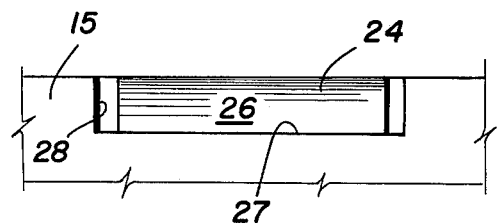
FIG. 6 is a sectional view of the invention taken on the line VI—VI of FIG. 5.

Both buttons are similar to the buttons 24 which, as is shown in FIGS. 5 and 6, consists of tapered, upwardly-directed surface 26 and a downwardly-directed undersurface 27. The insertion of the compartment element 15 into the aperture 14 causes the surface 16 of the compartment element to slide down the tapered surface 26. This squeezes the surface 16 and serves to slightly press the sides of the compartment together until the undersurface 27 of the button snaps over the upper edge of the element. The upper edge of the compartment element is provided with a notch 28 to receive the button, so that the upper edge of the compartment is on a level with the upper surface of the flange 13 of the main body.

Figure 4:
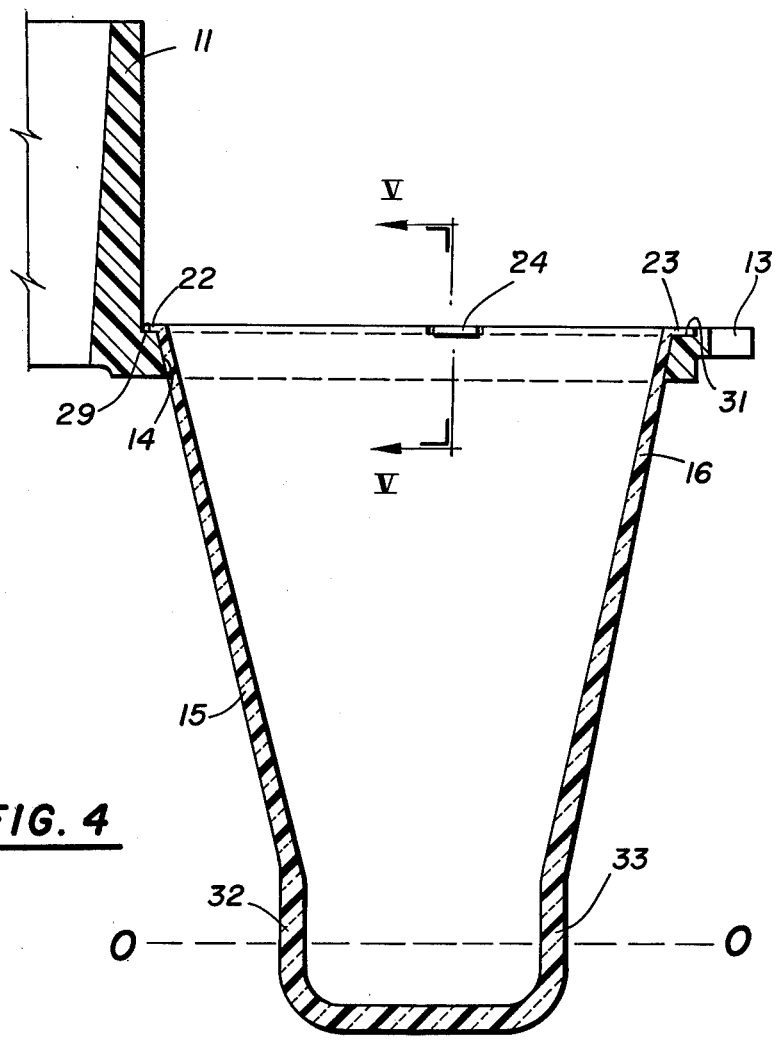
FIG. 4 is a vertical sectional view of a portion of the cuvette taken on the line IV—IV of FIG. 3.

A portion of the surface of the flange around the aperture 14 is provided with rabbets, including a rabbet 29 along the side 21 of the aperture and a rabbet 31 along the side 19 of the aperture. The flange 22 on the compartment element 15 fits in the rabbet 29, while the flange 23 fits in the rabbet 31. The outer peripheries of the rabbets and the flanges are substantially the same shape. As is evident in FIG. 4, the sides of the compartment element 15 are tapered downwardly to terminate in two parallel spaced portions 32 and 33 which present no optical aberration to an analysis viewing (light beam) along the line O—O, these walls being substantially polished to assure a good optical clarity. FIG. 3 shows clearly how the outer periphery of the flange 13 of the main body is provided with indexing, semi-circular notches 34 and the manner in which a numeral is engraved on the upper surface of the flange on each side of that notch, thus positively identifying each notch. One notch is located in the exact center of each aperture 19 and, in the preferred embodiment, there are 32 notches.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. A cuvette system for use on chemical analysis machine, using a beam of radiant energy for measurement, comprising:
   (a) a main body having a central bore to permit mounting on the machine for rotation about the axis of the bore and a flange extending radially outwardly in a general plane perpendicular to the axis, the flange being formed with a plurality of similar trapezoidal apertures at equal spacing about the axis,
   (b) a plurality of compartment elements formed of an optically-clear polymer, each element being in the form of an upwardly-opening container whose outer surface around the upper edge fits snugly in an aperture, and
   (c) means consisting of a pair of buttons located on opposite portions of each aperture is provided to lock the compartment element in the aperture to resist dislodgement therefrom.

2. A cuvette system as recited in claim 1, wherein each button consists of a tapered, upwardly-direction surface and a downwardly-directed undersurface, the insertion of the compartment element into the aperture causing the surfaces of the element to slide down the tapered surface, thus camming the walls of the element sideways, until the undersurface of the button snaps over the upper edge of the compartment element, the upper edge of the compartment element being provided with a notch to receive the button.

3. A cuvette system as recited in claim 1, wherein each aperture is in the general form of a trapezoid having elongated sides extending generally radially of the axis, a short base located outwardly of the flange, and an even shorter base located inwardly of the flange.

4. A cuvette system as recited in claim 1, wherein each compartment element is provided with an outwardly-extending ridge that rests on the surface of the flange along the edge of the aperture.

5. A cuvette system as recited in claim 1, wherein a portion of the surface of the flange around the aperture is provided with a rabbet, and wherein the upper portion of the compartment element has an outwardly-extending ridge that rests in the rabbet, the outer peripheries of the rabbet and the ridge being substantially the same.

6. A cuvette system as recited in claim 5, wherein the compartment element is tapered from the said upper portion to its bottom.

7. A cuvette system as recited in claim 6, wherein the lower portion of each compartment element has polished surfaces that are free of optical aberration.

8. A cuvette system for use on chemical analysis machine, using a beam of radiant energy for measurement, comprising:
   (a) a main body having a central bore to permit mounting on the machine for rotation about the axis of the bore and a flange extending radially outwardly in a general plane perpendicular to the axis, the flange being formed with a plurality of similar apertures at equal spacing about the axis,
   (b) a plurality of compartment elements formed of an optically-clear polymer, each element being in the form of an upwardly-opening container whose outer surface around the upper edge fits snugly in an aperture, and
   (c) means consisting of at least one abutment located on a portion of each aperture is provided to lock the compartment element in the aperture to resist dislodgement vertically therefrom.

9. A cuvette system as recited in claim 8, wherein the abutment consists of a tapered, upwardly-directed surface and a downwardly-directed undersurface, the insertion of the compartment element into the aperture causing the surface of the element to slide down the tapered surface, thus camming the walls of the element sideways, until the undersurface of the abutment snaps over the upper edge of the compartment element, the upper edge of the compartment element being provided with a notch to receive the abutment.

10. A cuvette system as recited in claim 8, wherein each aperture is in the general form of a trapezoid having elongated sides extending generally radially of the axis, a short base located outwardly of the flange, and an even shorter base located inwardly of the flange.

11. A cuvette system as recited in claim 8, wherein each compartment element is provided with an outwardly-extending ridge that rests on the surface of the flange along the edge of the aperture.

12. A cuvette system as recited in claim 8, wherein a portion of the surface of the flange around the aperture is provided with a rabbet, and wherein the upper portion of the compartment element has an outwardly-extending ridge that rests in the rabbet, the outer peripheries of the rabbet and the ridge being substantially the same.

13. A cuvette system as recited in claim 12, wherein the compartment element is tapered from the said upper portion to its bottom.

14. A cuvette system as recited in claim 13, wherein the lower portion of each compartment element has polished surfaces that are free of optical aberration.

* * * * *